United States Patent
Rashidi et al.

(10) Patent No.: US 12,125,314 B2
(45) Date of Patent: Oct. 22, 2024

(54) SYSTEMS AND METHODS FOR MACHINE LEARNING-BASED IDENTIFICATION OF SEPSIS

(71) Applicant: The Regents of the University of California, Oakland, CA (US)

(72) Inventors: Hooman H. Rashidi, Davis, CA (US); Nam K. Tran, Davis, CA (US)

(73) Assignee: The Regents of the University of California, Oakland, CA (US)

(*) Notice: Subject to any disclaimer, the term of this patent is extended or adjusted under 35 U.S.C. 154(b) by 431 days.

(21) Appl. No.: 17/635,972

(22) PCT Filed: Aug. 20, 2020

(86) PCT No.: PCT/US2020/047282
§ 371 (c)(1),
(2) Date: Feb. 16, 2022

(87) PCT Pub. No.: WO2021/035098
PCT Pub. Date: Feb. 25, 2021

(65) Prior Publication Data
US 2022/0292876 A1     Sep. 15, 2022

Related U.S. Application Data
(60) Provisional application No. 62/889,959, filed on Aug. 21, 2019.

(51) Int. Cl.
*G06V 40/16*     (2022.01)
*G06F 16/9535*     (2019.01)

(52) U.S. Cl.
CPC ........ *G06V 40/171* (2022.01); *G06F 16/9535* (2019.01)

(58) Field of Classification Search
CPC ......... G06T 11/60; G06T 7/0012; G06T 7/11; A61B 5/1566; A61B 5/72; A63F 13/52
See application file for complete search history.

(56) References Cited

U.S. PATENT DOCUMENTS 6,306,087 B1    10/2001    Barnhill et al.
7,742,641 B2 *    6/2010    Ivanov .................. G06F 18/256
                                                         382/190

(Continued)

FOREIGN PATENT DOCUMENTS

WO    WO-2017/165693 A1    9/2017

OTHER PUBLICATIONS

Kaji et al.; "An attention based deep learning model of clinical events in the intensive care unit"; Plos One; https://doi.org/10.1371/journal.pone.0211057; Feb. 13, 2019; 17 pages.

(Continued)

*Primary Examiner* — Yosef Kassa
(74) *Attorney, Agent, or Firm* — Volpe Koenig

(57) ABSTRACT

In some aspects, the disclosure is directed to methods and systems for machine learning-based identification of sepsis in patients, such as those with severe burn injuries. A set of biomarker and vital sign measurements of a population with a known clinical diagnosis may be collected and normalized. A first subset of the modified set of biomarker and vital sign measurements may be used to train and test the algorithm (e.g. a neural network), and a second subset of the modified set of biomarker and vital sign measurements may be used for secondary validation studies.

20 Claims, 9 Drawing Sheets

(56) References Cited

U.S. PATENT DOCUMENTS

| | | | | |
|---|---|---|---|---|
| 8,295,565 | B2* | 10/2012 | Gu | G06T 5/90 |
| | | | | 382/128 |
| 8,411,149 | B2* | 4/2013 | Maison | G06T 7/254 |
| | | | | 348/207.1 |
| 9,198,621 | B2* | 12/2015 | Fernstrom | A61B 5/1123 |
| 9,238,841 | B2 | 1/2016 | Wong et al. | |
| 9,332,953 | B2* | 5/2016 | Suzuki | A61B 6/032 |
| 10,885,629 | B2* | 1/2021 | Takada | A61B 5/4566 |
| 2017/0009297 | A1 | 1/2017 | Spencer et al. | |

OTHER PUBLICATIONS

US Patent and Trademark Office as International Searching Authority; International Search Report and Written Opinion; PCT/US2020/047282; dated Feb. 25, 2021; 10 pages.

International Preliminary Report on Patentability on PCT/US2020/047282 Dtd Mar. 3, 2022 (8 pages).

* cited by examiner

SYSTEMS AND METHODS FOR MACHINE LEARNING-BASED IDENTIFICATION OF SEPSIS

RELATED APPLICATIONS

The present application is a national stage application under 35 U.S.C. § 371 of International Application No. PCT/US2020/047282, filed Aug. 20, 2020, which in turn claims the benefit of and priority to U.S. Provisional Patent Application No. 62/889,959, entitled "Systems and Methods for Machine Learning-based Identification of Sepsis," filed Aug. 21, 2019, the entirety of each application is incorporated by reference herein.

FIELD OF THE DISCLOSURE

This disclosure generally relates to systems and methods for machine learning and artificial intelligence. In particular, this disclosure relates to systems and methods for machine learning-based early identification of sepsis in patients.

BACKGROUND OF THE DISCLOSURE

Current methods for detecting sepsis in patients rely on physician gestalt (which may be flawed), non-specific systemic inflammatory response syndrome (SIRS) criteria, and biomarkers. For example, the SIRS criteria may be met if a patient exhibits fever, has a rapid respiratory rate, has a high heart rate, and/or has abnormally high or low white blood cell counts. As a result, a healthy person can manifest SIRS just by exercising.

Sepsis is defined as SIRS with a suspected or identified source of infection. Unfortunately, infection is difficult to detect in a timely fashion using existing microbiological techniques, often taking 24-48 hours to provide definitive results. As a result, sepsis recognition may be delayed, contributing to its increased mortality—reported to be as high as 50% in some instances.

BRIEF DESCRIPTION OF THE DRAWINGS

The patent or application file contains at least one drawing executed in color. Copies of this patent or patent application publication with color drawings will be provided by the Office upon request and payment of the necessary fee.

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

The details of various embodiments of the methods and systems are set forth in the accompanying drawings and the description below.

DETAILED DESCRIPTION

For purposes of reading the description of the various embodiments below, the following descriptions of the sections of the specification and their respective contents may be helpful:

Section A describes embodiments of systems and methods for early recognition of sepsis via artificial intelligence and machine learning techniques; and Section B describes a computing environment which may be useful for practicing embodiments described herein.

A. Systems and Methods for Early Recognition of Sepsis Via Artificial Intelligence and Machine Learning Techniques Current methods for detecting sepsis in patients rely on physician gestalt (which may be flawed), non-specific systemic inflammatory response syndrome (SIRS) criteria, and biomarkers. For example, the SIRS criteria may be met if a patient exhibits fever, has a rapid respiratory rate, has a high heart rate, and/or has abnormally high or low white blood cell counts. As a result, a healthy person can manifest SIRS just by exercising. As a result, sepsis diagnoses may be prone to both false positives and false negatives.

For example, patients with severe burn injuries have lost their primary barrier to the environment and thus experience higher rates of infection, and the majority of burn related deaths for inpatients is due to sepsis. Early recognition of sepsis may be crucial for improving outcomes, but because existing microbiological techniques may take 24-48 hours to provide definitive results, sepsis can go untreated for long periods.

Although primarily discussed in terms of sepsis from burn injuries, the systems and methods discussed herein may be applied to diagnosis and treatment of sepsis from any source, including as a result of injury, infection, or any other indication. Patients and/or test subjects may be drawn from any suitable population, including burn patients, trauma patients, kidney transplant patients, surgery patients, patients in intensive care units, oncology patients, cardiology patients, elderly patients, infants or newborn patients, diabetic patients, patients with chronic kidney disease, or any other population or subgroup.

An optimized machine learning system may be used identify culture-positive sepsis, using a combination of laboratory and vital sign data. The machine learning system may be optimized through automated generation of large numbers (e.g. thousands) of models, including varying hyperparameter settings and values (e.g. variable activation functions, variable hidden layer depths, varying alpha values, etc.), and application of a plurality of machine learning algorithms to find a best performing model. In testing, the optimized machine learning system was able to adequately predict sepsis with novel variables compared to those recommended in consensus guidelines.

Figure 1:
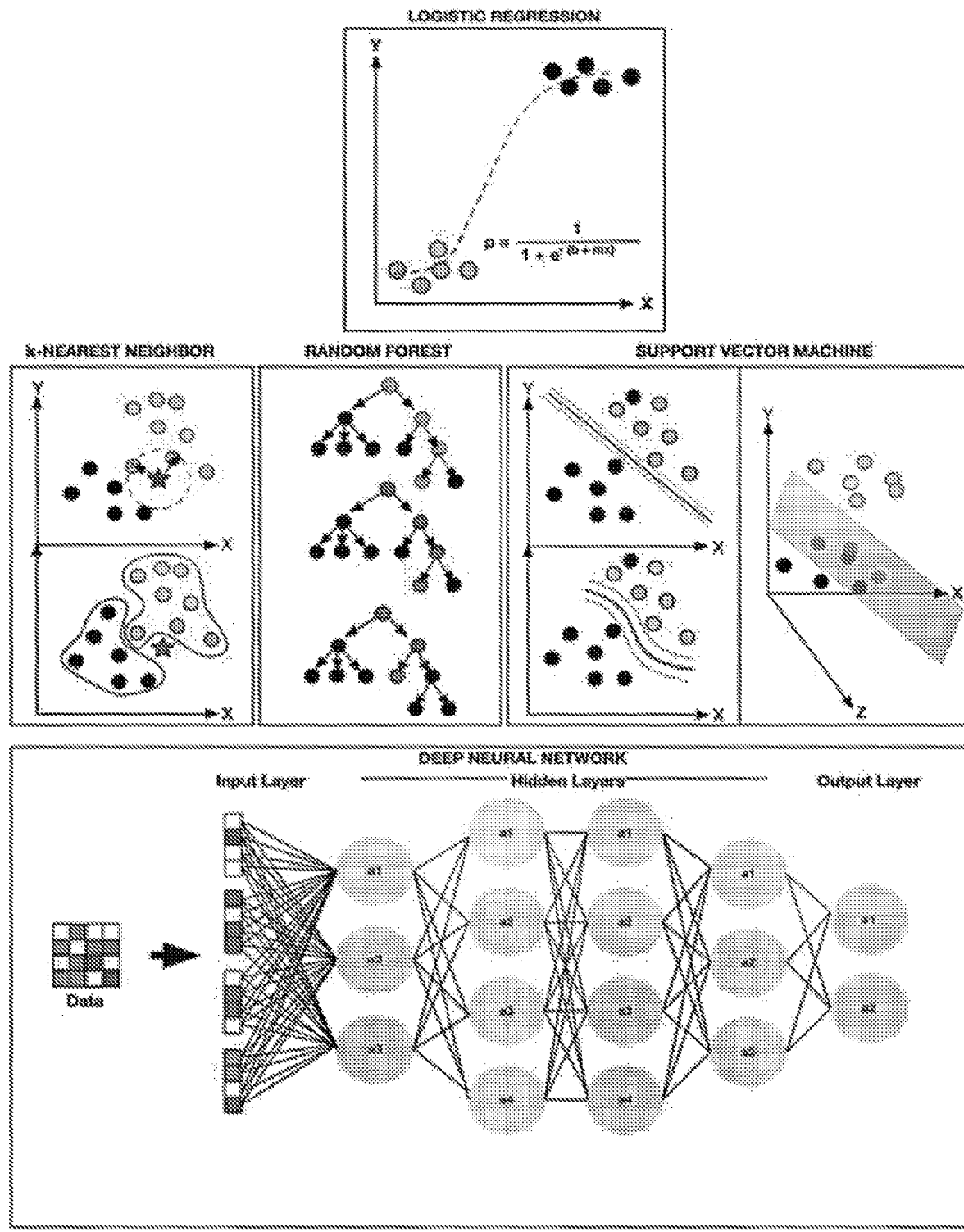
FIG. 1 is an illustration of various implementations of artificial intelligence/machine learning approaches.

Various artificial intelligence and machine learning (AI/ML) approaches, illustrated in FIG. 1, were utilized to optimize the system and differentiate between sepsis and non-sepsis patients. The figure compares the five AI/ML techniques analyzed, illustrated as conceptual drawings. These techniques included: (a) logistic regression (LR), (b) k-nearest neighbor (k-NN), (c) random forest (RF), (d) support vector machine (SVM), and a multi-layer perceptron (MLP) deep neural network (DNN), as shown in FIG. 1.

Briefly, LR is based on traditional statistical techniques identifying predictors of a binary outcome (e.g., sepsis vs. non-sepsis). k-NN is a non-parametric pattern recognition algorithm used for classification and regression. Classification is based on the number of k neighbors and its Euclidean distance (d) from a pre-defined point. In contrast, random forest, a form of ensemble learning, uses a multitude of constructed decision trees for classification and regression. Next, SVM is a form of AI/ML that classifies data by defining a hyperplane that best differentiates two groups (e.g., sepsis vs. non-sepsis patients) by maximizing the margin (the distance), ultimately leading to a hyperplane-bounded region with the largest possible margin. Thus, the goal of SVM is to maximize the distance (margin) between groups of data which can also be applied as a linear method to nonlinear data by transposing the data features into a higher dimension (e.g., three dimensions) through the use of kernels. This ultimately allows for a better classification and differentiation of the groups of interest (e.g., sepsis vs. non-sepsis). Lastly, DNN utilizes artificial neural networks with multiple levels between input and output layers. Ultimately these multi-layer perceptrons (MLP) within the DNN identifies the appropriate mathematical manipulation to convert an input into an output.

To generate and validate an optimized model, the system may generate a large number of models for each machine learning approach using various hyperparameters settings and combinations of data inputs/features within the various algorithms employed (see FIG. 1). An example of one such model is a custom multi-layer neural network grid search. In some such implementations, a stochastic gradient-based optimizer was used within the custom multi-layer neural networks along with a grid search with variable number of hidden layers, variable penalty regularization alpha parameters, variable tol values (tolerance for the optimization parameters) and two unique activation functions: ReLU (the rectified linear unit function) and tanh (hyperbolic tan function) to find the best performing multi-layer neural network for each category.

Figure 2:
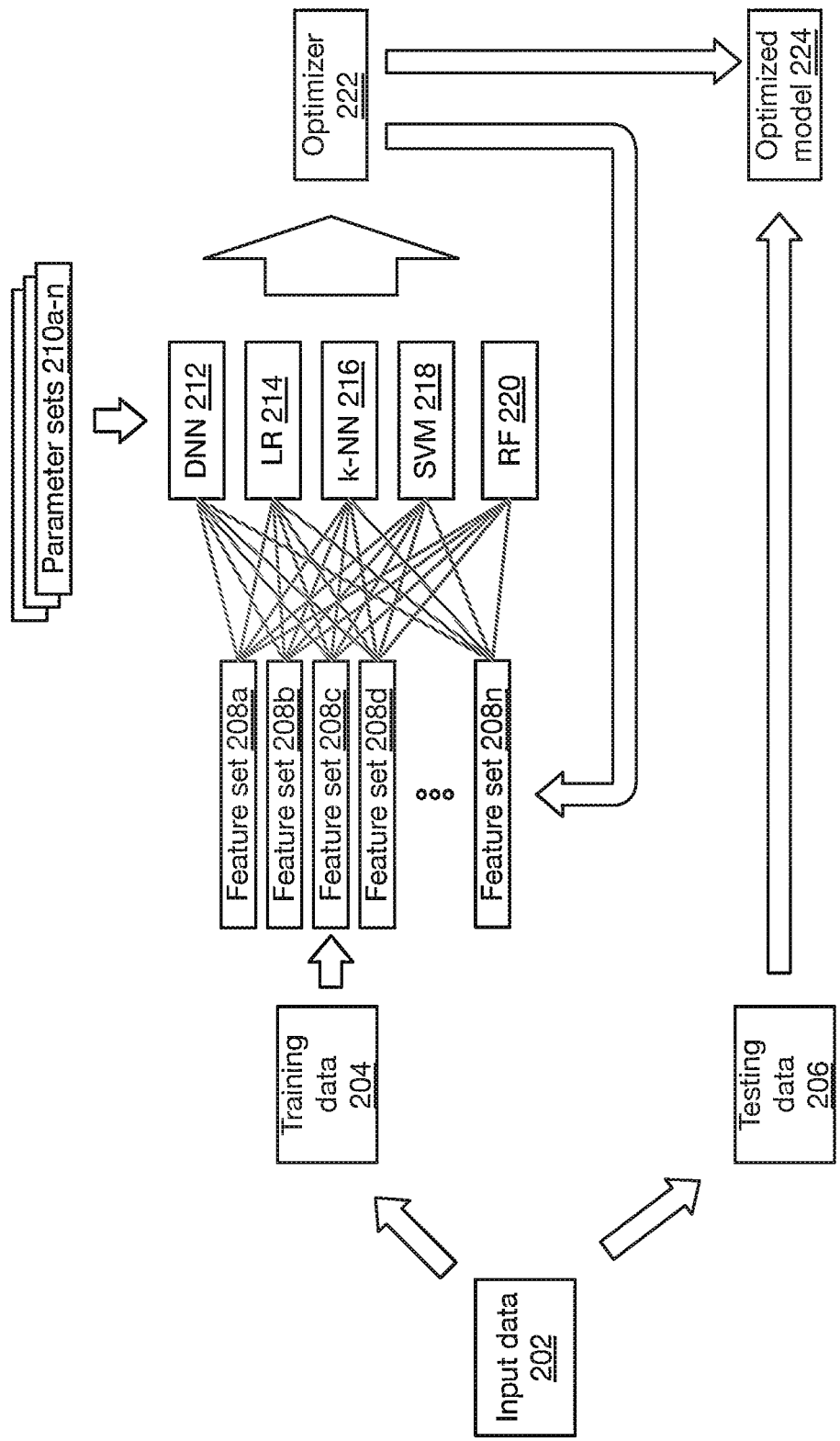
FIG. 2 is a block diagram of a system for generation of an optimized machine learning model.

For example, referring briefly to FIG. 2, illustrated is a block diagram of a system for generation of an optimized machine learning model. Input data 202, which may be gathered from hundreds or thousands of unique patient reports, may be divided into training data 204 and testing data 206 (e.g. 90% training data, and 10% testing data, or any other such division). In some implementations, such as where a given patient is initially sepsis-negative and later is sepsis-positive, data from both conditions may be used. The data 202 may be in any appropriate form or data structure, and may include values for one or more laboratory and vital sign data, including:

aPTT Activated Partial Thromboplastin Time
BUN Blood urea nitrogen
Chloride Plasma Chloride
Creatinine Plasma Creatinine
CVP Central Venous Pressure
D-Dimer D-dimer concentration
DBP Diastolic Blood Pressure
FiO2 Fraction of inspired O2
GCS Glasgow Coma Score
Glucose Plasma Glucose
HCO3 Bicarbonate
HCT Hematocrit
HR Heart Rate
INR International normalized ratio
K+ Potassium
MAP Mean Arterial Pressure
Na+ Sodium
PaCO2 Partial pressure of arterial CO2
PaO2 Partial pressure of arterial O2
pH pH status
Platelet Platelet count
PT Prothrombin time
RR Respiratory Rate
SBP Systolic Blood Pressure
Tbil Total Bilirubin
TCO2 Total CO2
Temp Temperature
Vent Ventilator status
WBC White blood cell count In many instances, the laboratory and vital sign data may be incomplete or sparse (e.g. some data may not exist for any given patient record). The data may be divided into patients who have been proven to have sepsis and patients who have been proven to have had no sepsis.

While a large variety of biomarker data or features may be obtained, as shown above, some of this data may be more relevant or important to identifying sepsis than other data. To automatically identify the relevant features, in some implementations, a system may extract a number of feature sets (208a-208n) from the training data 204, which may comprise a subset of the biomarker data. For example, as discussed in more detail below, a subset of features may provide sufficient accuracy and sensitivity to sepsis diagnosis while requiring fewer laboratory tests and reduced time and resources.

However, various feature sets may result in different accuracies or sensitivities when used with different ML/AI algorithms (e.g. deep neural network 212, logistic regression 214, k-nearest neighbor 216, support vector machine 218, and random forest 220). Accordingly, to generate and validate an optimized model 224, an optimizer 222 of the machine learning system may generate a large number of models comprising different feature sets 208a-208n and different hyperparameter sets 210a-210n (e.g. coefficients or weights for the various models, including c values, gamma values, etc., for each ML algorithm) and apply a grid search cross validation analysis to identify the best performing combination of model and ML algorithm. For example, in one such implementation, data from 500 reports (consisting of 250 sepsis patient reports and 250 non-sepsis patient reports) were used for training models, with 454 combinations of various hyperparameters and values, creating 10 runs for each specific feature set and hyperparameter combination, and applied to each ML algorithm, resulting in 4540 models. To expand this further, some feature sets included all of the biomarker data, while other feature sets included a subset, selected from the n most relevant or top contributing features of a larger subset. For example, a first feature set may include all of the biomarker data, while a second feature set may include the top 20 features that contributed most to the classification of patients from the first feature set (e.g. selecting features according to a pre-determined threshold percentile of the highest scores for each feature, or a univariant feature selection process). Thus, the model building process may be iterative in many implementations, with output data from a first iteration used to filter or extract features for a further feature set in a second iteration. In the implementation discussed above, 11 feature sets were used with the training models, with one feature set including all biomarkers, and each of the other ten feature sets comprising a subset of features, selected from the top performing features of the previous feature set to exclude the worst performing two features, resulting in 49,940 models or combinations of feature sets and hyperparameters for each of the 10 training runs (e.g., k-fold=10 cross validation).

The mean accuracy (Acc, in percentage), standard deviation (SD), and mean area under the curve (AUC) for the best model generated for each feature set were determined, and are listed below:

TABLE 1

Training Data analysis results

|  | Neural Network | | Logistic Regression | | k-Nearest Neighbor Categories | | Support Vector Machine | | Random Forest | |
| --- | --- | --- | --- | --- | --- | --- | --- | --- | --- | --- |
|  | ACC & SD | AUC/SD | ACC & SD | AUC/SD | ACC & SD | AUC/SD | ACC & SD | AUC/SD | ACC & SD | AUC/SD |
| All Features | 79 | 68 | 74 | 72 | 76 | 63 | 79 | 55 | 79 | 82 |
|  | 7 | 8 | 6 | 7 | 7 | 12 | 5 | 4 | 7 | 7 |
| Top 20 features | 78 | 68 | 74 | 73 | 75 | 57 | 75 | 53 | 77 | 80 |
|  | 5 | 11 | 6 | 6 | 7 | 12 | 7 | 5 | 5 | 8 |
| Top 18 features | 77 | 65 | 74 | 74 | 75 | 58 | 75 | 56 | 77 | 80 |
|  | 5 | 7 | 7 | 7 | 4 | 10 | 9 | 10 | 5 | 8 |
| Top 16 features | 77 | 68 | 74 | 73 | 75 | 60 | 76 | 53 | 77 | 80 |
|  | 6 | 10 | 7 | 9 | 7 | 11 | 6 | 6 | 6 | 8 |
| Top 14 features | 77 | 72 | 74 | 75 | 76 | 60 | 77 | 62 | 77 | 80 |
|  | 5 | 9 | 7 | 8 | 5 | 8 | 5 | 8 | 6 | 8 |
| Top 12 features | 76 | 70 | 76 | 78 | 75 | 67 | 76 | 62 | 77 | 81 |
|  | 6 | 11 | 7 | 9 | 5 | 7 | 6 | 6 | 6 | 8 |
| Top 10 features | 76 | 73 | 76 | 78 | 72 | 70 | 75 | 64 | 76 | 81 |
|  | 4 | 8 | 7 | 9 | 5 | 9 | 7 | 9 | 7 | 7 |
| Top 8 features | 78 | 74 | 76 | 80 | 74 | 72 | 77 | 62 | 77 | 78 |
|  | 7 | 9 | 8 | 9 | 5 | 9 | 7 | 6 | 7 | 8 |
| Top 6 features | 77 | 74 | 77 | 82 | 73 | 72 | 76 | 65 | 76 | 83 |
|  | 7 | 10 | 8 | 7 | 8 | 9 | 7 | 8 | 7 | 6 |
| Top 4 features | 75 | 68 | 73 | 78 | 73 | 69 | 75 | 63 | 75 | 80 |
|  | 6 | 12 | 9 | 9 | 6 | 9 | 7 | 6 | 7 | 7 |
| Top 2 features | 73 | 67 | 70 | 77 | 70 | 70 | 72 | 72 | 70 | 75 |
|  | 8 | 12 | 8 | 11 | 10 | 12 | 8 | 11 | 8 | 11 |

To validate the models, additional testing data 206 that was not previously seen by the algorithms was tested against the best model (hyperparameter values and feature combinations) for each ML algorithm. The accuracy, sensitivity (Sen), specificity (Spc), and AUC for each is listed below in Table 2A and 2B:

TABLE 2A

Testing Data analysis results (Neural Network, Logistic Regression, k-Nearest Neighbor)

|  | Neural Network | | | Logistic Regression Categories | | | k-Nearest Neighbor | | |
| --- | --- | --- | --- | --- | --- | --- | --- | --- | --- |
|  | Acc | Sen/Spc | AUC | Acc | Sen/Spc | AUC | Acc | Sen/Spc | AUC |
| All Features | 77 | 88 73 | 80 | 81 | 96 76 | 86 | 70 | 81 66 | 74 |
| Top 20 features | 75 | 98 69 | 83 | 83 | 98 78 | 88 | 68 | 90 62 | 76 |
| Top 18 features | 78 | 92 73 | 82 | 82 | 98 78 | 88 | 69 | 90 62 | 76 |
| Top 16 features | 76 | 98 69 | 84 | 86 | 98 82 | 90 | 77 | 98 71 | 85 |
| Top 14 features | 77 | 98 70 | 84 | 83 | 98 79 | 88 | 71 | 88 66 | 77 |
| Top 12 features | 79 | 96 74 | 85 | 82 | 96 78 | 87 | 71 | 88 66 | 77 |
| Top 10 features | 80 | 96 76 | 86 | 81 | 96 76 | 86 | 81 | 98 76 | 87 |
| Top 8 features | 77 | 96 72 | 84 | 79 | 96 74 | 85 | 79 | 98 74 | 86 |
| Top 6 features | 77 | 98 71 | 84 | 78 | 96 73 | 84 | 81 | 96 76 | 86 |

TABLE 2A-continued

Testing Data analysis results (Neural Network, Logistic Regression, k-Nearest Neighbor)

| | Neural Network | | | Logistic Regression Categories | | | k-Nearest Neighbor | | |
|---|---|---|---|---|---|---|---|---|---|
| | Acc | Sen/Spc | AUC | Acc | Sen/Spc | AUC | Acc | Sen/Spc | AUC |
| Top 4 features | 74 | 88 70 | 79 | 74 | 85 71 | 78 | 78 | 81 78 | 79 |
| Top 2 features | 79 | 67 84 | 75 | 75 | 69 75 | 72 | 78 | 75 79 | 77 |

TABLE 2B

Testing Data analysis results (SVM, Random Forest)

| | Support Vector Machine Categories | | | Random Forest | | |
|---|---|---|---|---|---|---|
| | Acc | Sen/Spc | AUC | Acc | Sen/Spc | AUC |
| All Features | 72 | 94 65 | 79 | 77 | 94 72 | 83 |
| Top 20 features | 67 | 81 63 | 72 | 77 | 94 72 | 83 |
| Top 18 features | 84 | 98 79 | 89 | 79 | 94 74 | 84 |
| Top 16 features | 73 | 94 67 | 80 | 78 | 90 74 | 82 |
| Top 14 features | 85 | 98 81 | 89 | 79 | 92 76 | 84 |
| Top 12 features | 79 | 96 74 | 85 | 78 | 92 74 | 83 |
| Top 10 features | 69 | 77 67 | 72 | 78 | 92 74 | 83 |
| Top 8 features | 72 | 92 66 | 79 | 73 | 88 68 | 78 |
| Top 6 features | 78 | 96 73 | 84 | 74 | 96 67 | 82 |
| Top 4 features | 77 | 83 75 | 79 | 74 | 88 70 | 79 |
| Top 2 features | 79 | 73 81 | 77 | 73 | 79 71 | 75 |

As shown emphasized above, the accuracy, sensitivity, specificity, and AUC values were highest for the logistic regression algorithm, with a subset of the top 16 features identified from the biomarker data. Sensitivity was important for sepsis detection, as patient outcomes depend on catching patients with severe sepsis early. The logistic regression algorithm-based best performing model had the highest specificity and high sensitivity, with very high accuracy. The 16 features utilized were mean arterial pressure; respiratory rate; temperature; Glasgow Coma Score; white blood cell count; hemoglobin; hematocrit; platelet count; sodium; potassium; blood urea nitrogen; creatinine; blood urea nitrogen/creatinine ratio; glucose; total CO2; and multiple organ dysfunction calculator score. The additional features excluded as a result of the iteration included activated partial thromboplastin time, plasma chloride, anion gap, central venous pressure, D-dimer concentration, diastolic and systolic blood pressure, O2 saturation, fraction of inspired O2, bicarbonate, heart rate, international normalized ratio, pH status, prothrombin time, total bilirubin, and ventilator status.

Figure 3A:
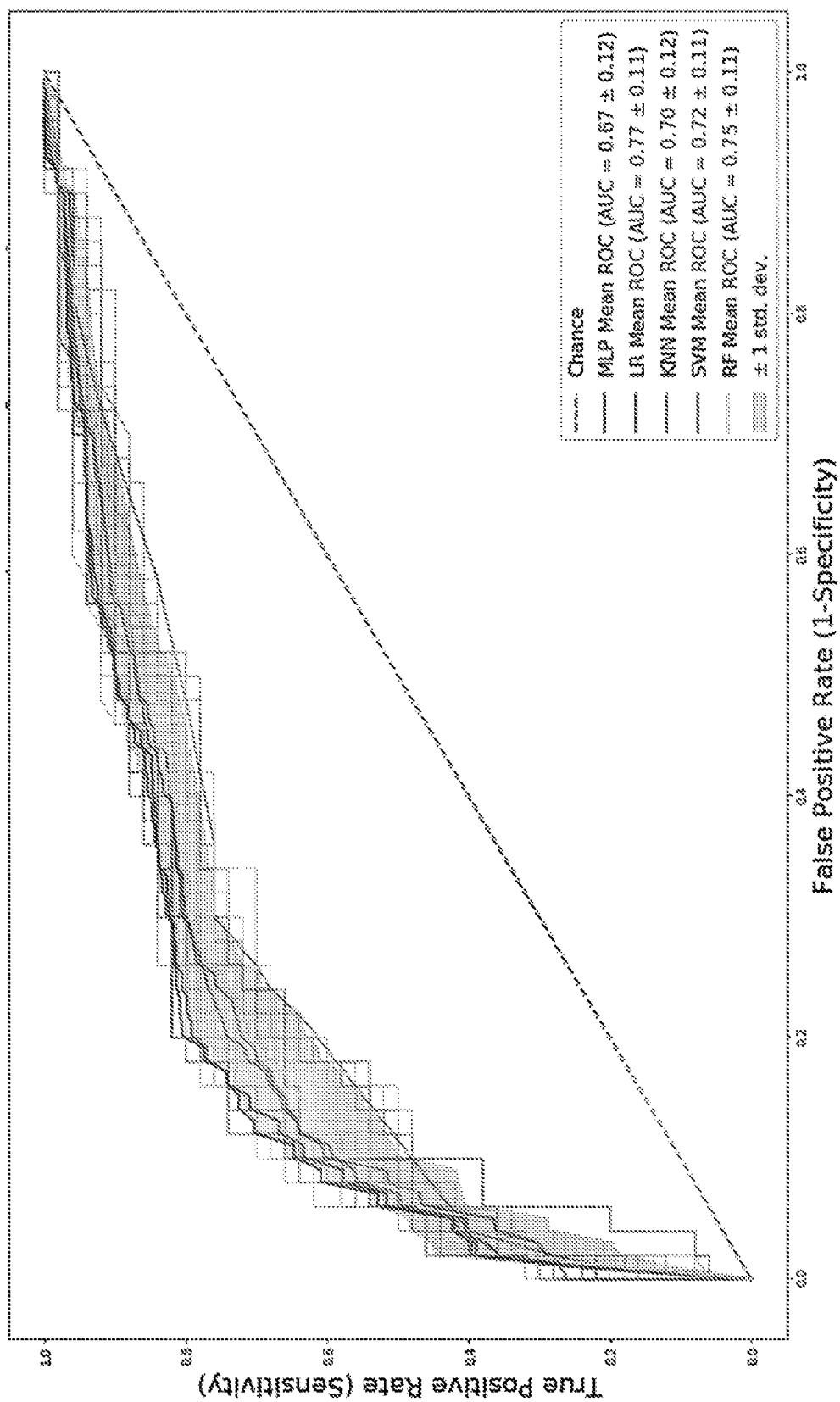
FIG. 3A-3C are illustrations comparing receiver operating characteristic (ROC) curves and average area under the curve (AUC) for each of a plurality of machine learning models.
Figure 3B:
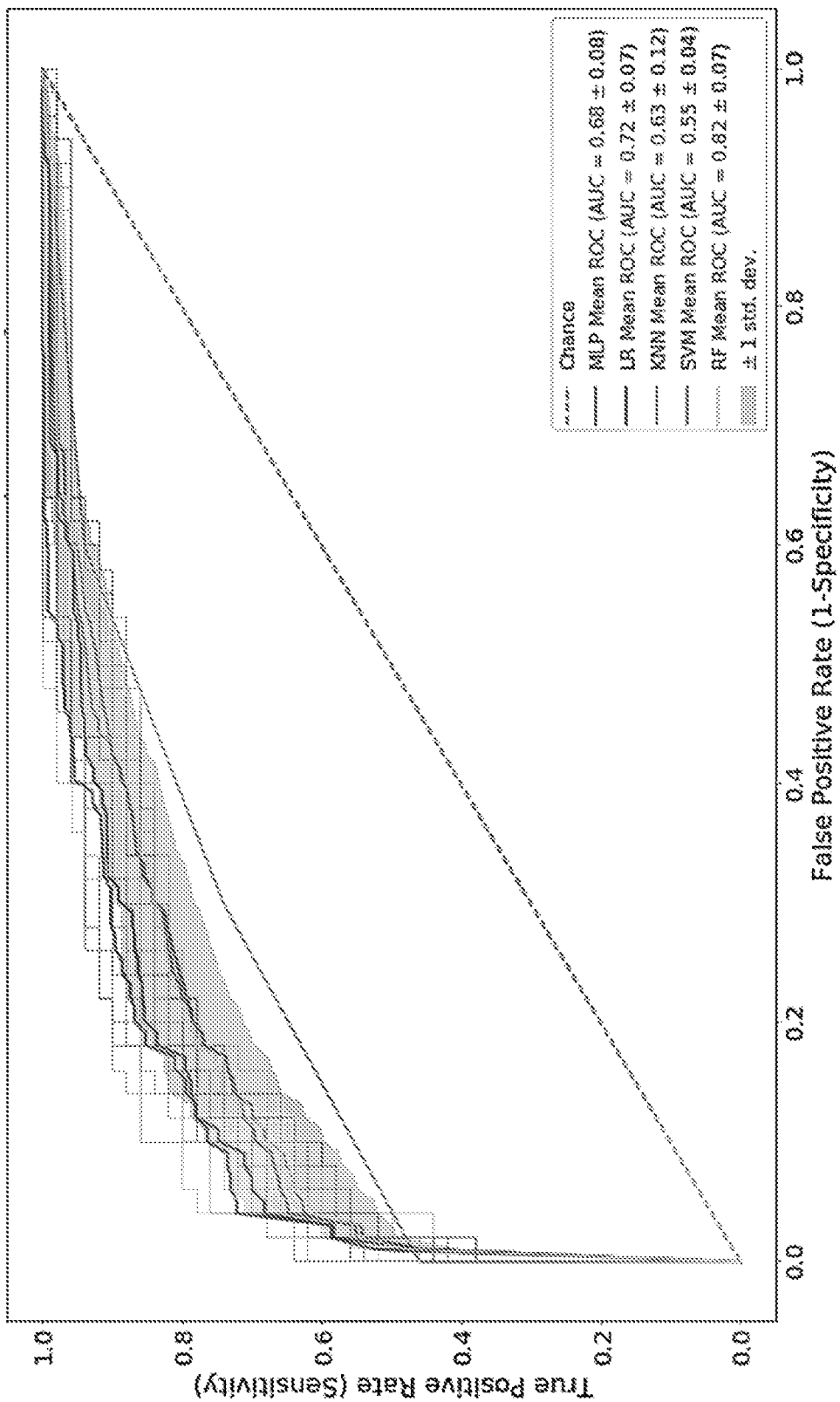
Figure 3C:
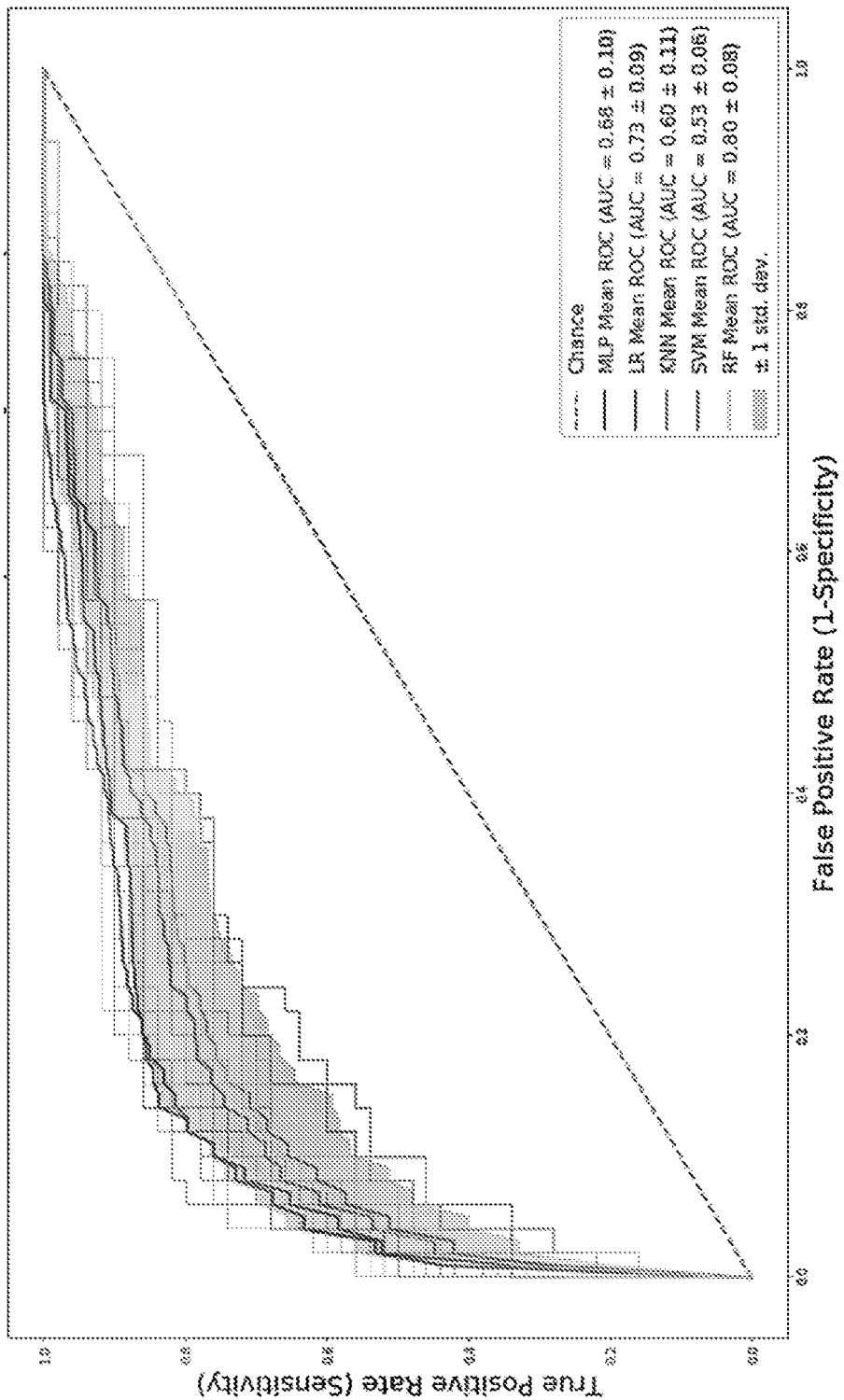

FIGS. 3A-3C are illustrations comparing receiver operating characteristic (ROC) curves and average area under the curve (AUC) for each of a plurality of machine learning models. These figures compare the best ROC curves for each AI/ML technique with differing combinations of biomarkers. False positive rate (1–specificity) and true positive rates (sensitivity) are reported on the x- and y-axis respectively. FIG. 3A illustrates sensitivity and specificity for models using the k-best top 2 features from the biomarkers, specifically temperature and blood urea nitrogen. FIG. 3B illustrates sensitivity and specificity for models using all of the biomarkers. FIG. 3C illustrates sensitivity and specificity for models using the k-best top 16 features, discussed above. As shown, and as discussed above in connection with table 2A, the use of feature subsets may increase sensitivity and specificity by excluding noisy or less relevant biomarkers, allowing for improved detection and diagnosis while reducing the laboratory and physician resources needed.

Figure 4:
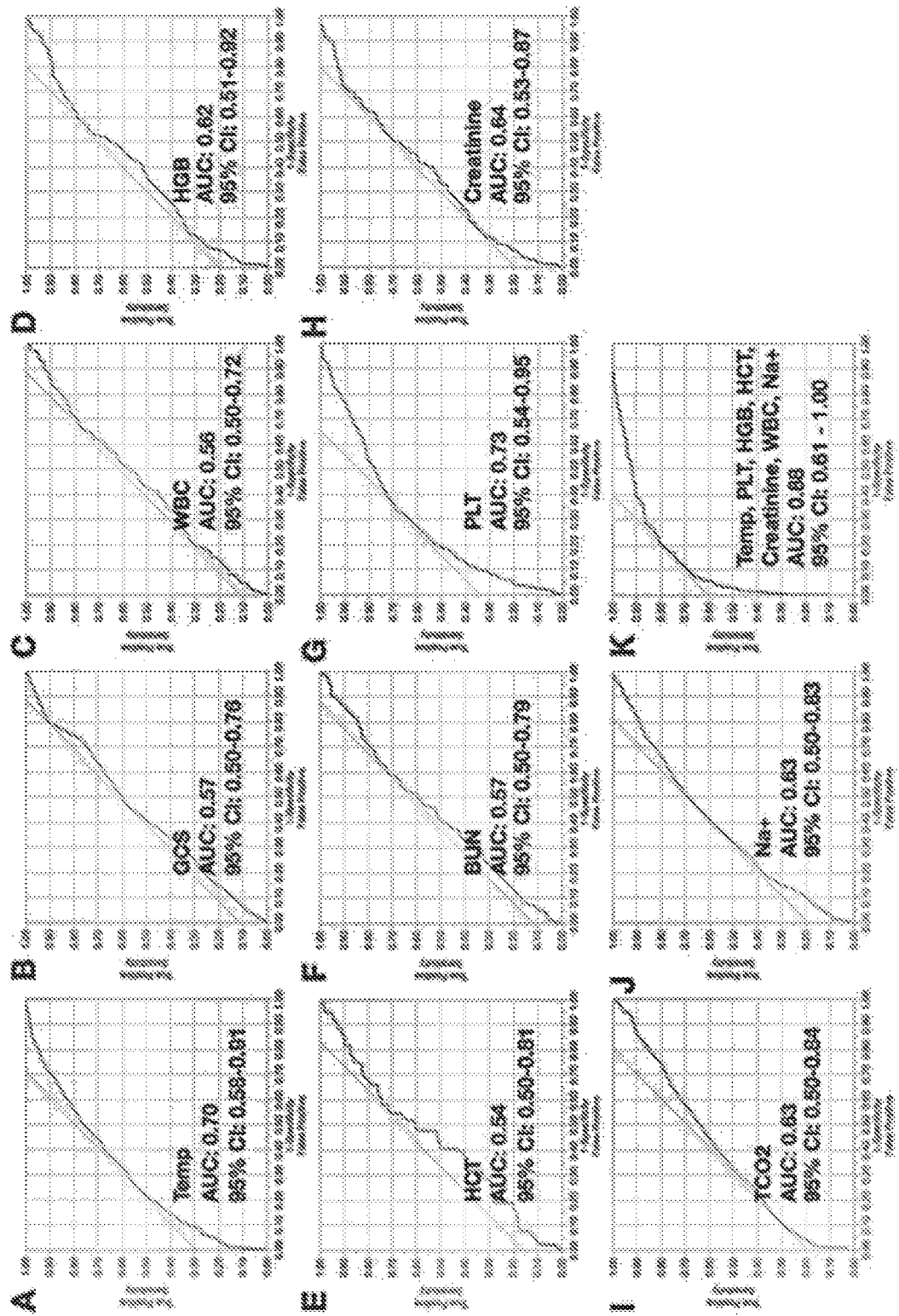
FIG. 4 is a set of graphs of receiver operator characteristic curves for statistically significant burn sepsis biomarkers identified via an optimized machine learning model.

FIG. 4 is a set of graphs of receiver operator characteristic (ROC) curves for statistically significant burn sepsis biomarkers (BUN blood urea nitrogen, GCS Glasgow coma score, HCT hematocrit, HGB hemoglobin, Na+ sodium, PLT platelet, TCO2 total carbon dioxide) identified via an optimized machine learning model. (A-J) represent the ROC curves and the area under the curve (AUC) analysis (in fractions) with 95% confidence intervals (CI) for statistically significant predictors of burn sepsis. (K) is the ROC curve for a multivariate model that predicts sepsis using logistic regression, according to some implementations. The tangent line for each ROC curve identifies the point where sensitivity and specificity are optimized.

Figure 5:
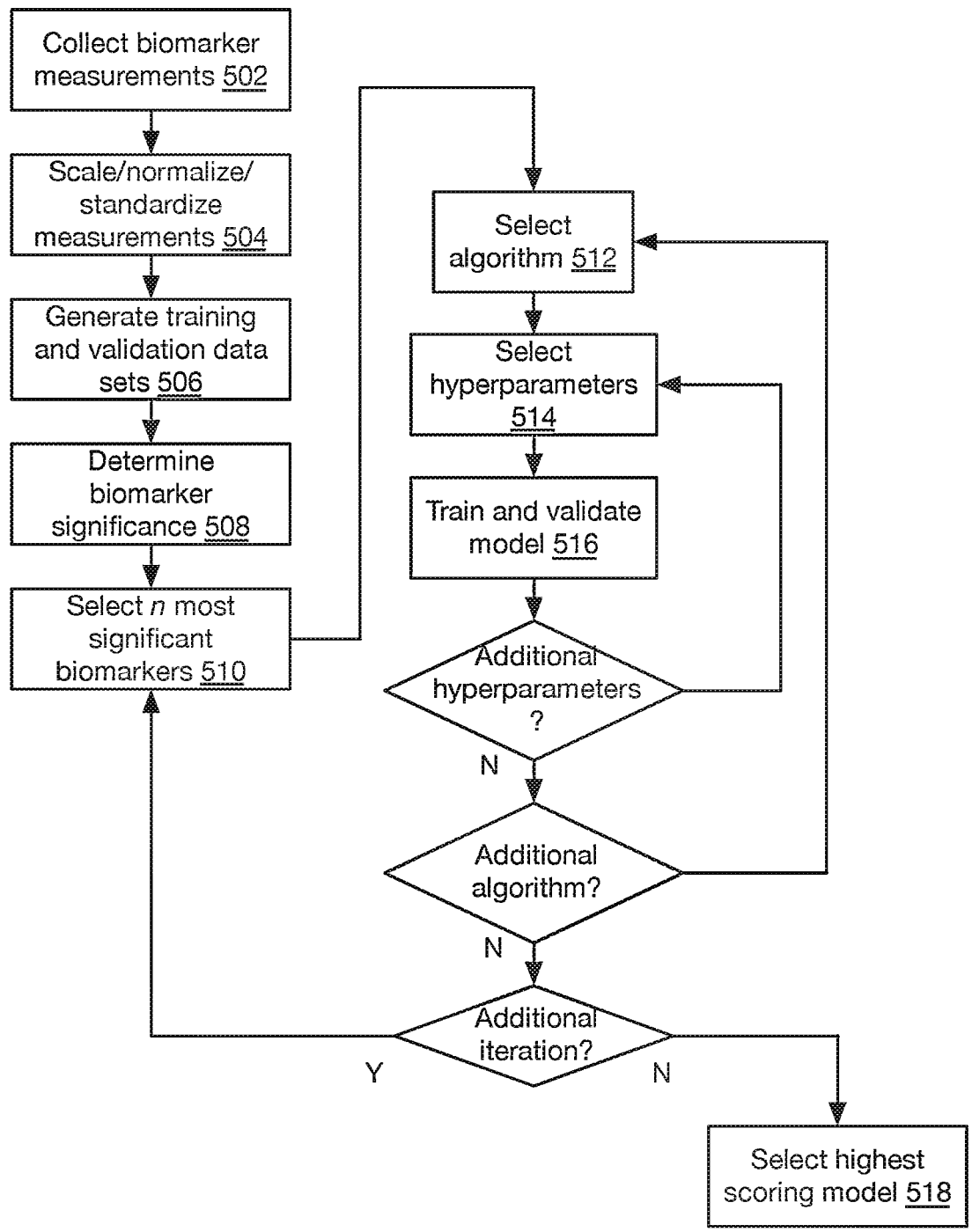
FIG. 5 is a flow chart of a method for training machine learning systems for early recognition of sepsis, according to some implementations.

FIG. 5 is a flow chart of a method for training machine learning systems for early recognition of sepsis, according to some implementations. At step 502, a computing device may receive, retrieve, or otherwise collect a set of biomarker and vital sign measurements of a population with a known clinical diagnosis. The measurements may comprise, for example, biomarker and vital measurements of a first set of subjects diagnosed as having sepsis and a second set of subjects determined to not have sepsis, and may be collected from medical records, clinical study populations, etc. The measurements may be received in any suitable format, such as an array, a comma-separated value string, a database, a spreadsheet, or any other such data structure.

At step 504, in some implementations, the computing device may transform the collected set of measurements. As discussed above, in many implementations, measurements may be incomplete or partial (e.g. missing one or more values for a set of measurements for a subject). In some such implementations, such incomplete or partial measurements may be filtered from the data set. Similarly in many implementations, measurements may be in different scales or ranges, and may be normalized or scaled to a predetermined range. For example, some measurements may be according to predetermined score ranges (e.g. GCS), while other measurements are percentages, or concentrations. To allow for more efficient comparison and to avoid large ranges dominating over smaller ranges, measurements may be scaled to a predetermined range (e.g. 1-100, 0-1, etc.).

At step 506, the computing device may divide the collected (and potentially modified or transformed) measurements into a first training set and a second validation set. The training set may be balanced in many implementations (e.g. having equal numbers of samples having a known clinical diagnosis and those known to not have the clinical diagnosis). The validation set may be balanced or unbalanced, in many implementations.

At step 508, in some implementations, the computing device may determine a significance score for each biomarker. Determining the score may comprise performing a feature analysis, such as a principal component analysis or similar technique, to determine a relative significance of each score.

At step 510, in some implementations, a subset of the biomarkers may be selected such as the n most significant markers or those having the n highest significance scores (e.g. 5 biomarkers, 10 biomarkers, 15 biomarkers, 20 biomarkers, or any other such value).

At step 512, a machine learning algorithm may be selected, such as a deep neural network, logistic regression, naïve Bayes, k-nearest neighbor, support vector machine, random forest, or XGBoost gradient boosting machine (GBM), or any other similar algorithms or classifiers. At step 514, a set of hyperparameters may be selected for the algorithm (e.g. corresponding to parameters used by the algorithm, such as a number of hidden layers, starting coefficients, learning rates, regularization value, etc. At step 516, a model may be generated using the algorithm, selected hyperparameter values, and the first set of training data. For example, in some implementations, the model may be trained by calculating a distance from a selected measurement of the subset for each of a plurality of measurements of the subset; sorting each of the plurality of measurements of the subset based on an increasing order of distance from the selected measurement of the subset; and classifying a further subset of the subset based on the sorted distance as belonging to a first class. This classification may be used in a supervised learning process to classify other samples and compare with known labels for false positives or negatives. In some implementations, the model may be validated using the second set of validation data (e.g. comparing an accuracy or sensitive to a validation threshold).

As shown, steps 510-514 may be repeated iteratively for a plurality of hyperparameter values for a given algorithm, for a plurality of algorithms, and for a plurality of different subsets of biomarkers (e.g. 10 biomarkers with hyperparameters a, b, c for a first machine learning system; 5 biomarkers with the same parameters and machine learning system; the original 10 biomarkers with hyperparameters d, e, f for the first machine learning system; the ten biomarkers for a second machine learning system with hyperparameters g, h, i, etc.). As discussed above, the hyperparameter selections may be according to a grid search or random search in various implementations to cover a given range of values. Because training and validation of one combination of biomarkers, algorithm, and hyperparameter values is not dependent on another, this process may be easily scaled amongst a plurality of parallel processing units or computing devices, with the results (e.g. accuracy and/or sensitivity scores for each combination) aggregated at a controller or master computing device. The highest performing combination may be selected at step 518 and utilized for classifying other data, such as diagnosis of sepsis in a new subject. The classification of a subject as having or not having sepsis may be used to selectively apply or not apply further treatments (e.g. treatments which may be harmful to non-septic patients), such as treating a subject diagnosed as septic via the machine learning system via plasmapheresis or plasma exchange. As discussed above, in one implementation and a study population, a machine learning system utilizing a k-NN classifier with biomarkers consisting of a heart rate, a body temperature, a hemoglobin (HGB) count, a blood urea nitrogen (BUN) count, and a total carbon dioxide (TCO2) count was determined to have the highest performance metrics, and accordingly such a system may be utilized for early stage diagnosis and treatment.

Thus, according to the systems and methods discussed herein, AI/ML models may be used for analysis and prediction of sepsis. In many implementations, logistic regression models on a subset of biomarker features may provide the best generalization accuracy and balance between sensitivity/specificity.

In one aspect, the present disclosure is directed to a method for training machine learning systems for early recognition of sepsis. The method includes collecting, by a computing device, a set of biomarker and vital sign measurements of a population with a known clinical diagnosis. The method also includes applying, by the computing device, one or more transformations to each biomarker and vital sign measurement including standardization to create a modified set of biomarker and vital sign measurements. The method also includes creating, by the computing device, a first training set comprising a subset of the modified set of biomarker and vital sign measurements. The method also includes training, by the computing device, a machine learning system using the first training set. The method also includes validating, by the computing device, the machine learning system using a second subset of the modified set of biomarker and vital sign measurements as a test set.

In some implementations, the method includes, for each of a plurality of measurements of the subset, calculating a distance from a selected measurement of the subset; sorting each of the plurality of measurements of the subset based on an increasing order of distance from the selected measurement of the subset; and classifying a further subset of the subset based on the sorted distance as belonging to a first class. In a further implementation, the method includes using the classification of the further subset for a supervised learning process.

In some implementations, the method includes filtering samples from the collected set having incomplete biomarker or vital sign measurements. In some implementations, the method includes training a plurality of machine learning systems with the first training set, and selecting a highest performing machine learning system of the plurality of machine learning systems. In a further implementation, the method includes providing a first subset of the biomarker and vital sign measurements to a first machine learning system of the plurality of machine learning systems, and providing a different second subset of the biomarker and vital sign measurements to a second machine learning system of the plurality of machine learning systems. In a still further implementation, the first machine learning system and second machine learning system have identical hyperparameters. In another further implementation, training the plurality of machine learning systems further comprises providing a first subset of the biomarker and vital sign measurements to each of a first machine learning system and a second machine learning system having different hyperparameters than the first machine learning system.

In some implementations, the method includes selecting a first subset of the biomarker and vital sign measurements having a first known clinical diagnosis and a second subset of the biomarker and vital sign measurements having a second known clinical diagnosis, the second subset equal in number to the first subset.

In another aspect, the present disclosure is directed to a computing device comprising a processor executing a machine learning system trained according to the above discussed methods. In still another aspect, the present disclosure is directed to a method for machine learning-based identification of sepsis, comprising receiving, by a machine learning system trained according to the methods discussed above, a set of biomarker and vital sign measurements of a subject; and classifying, by the machine learning system, the subject as having sepsis. In some implementations, the machine learning system comprises a k-nearest neighbor (k-NN) classifier, a neural network, a gradient boosting machine, a support vector machine, a logistic regression classifier, a naïve Bayes classifier, or a random forest classifier. In some implementations, the set of biomarker and vital sign measurements of the subject consists essentially of measurements of a heart rate, a body temperature, a hemoglobin (HGB) count, a blood urea nitrogen (BUN) count, and a total carbon dioxide (TCO2) count.

In another aspect, the present disclosure is directed to a method for training machine learning systems for early recognition of sepsis. The method includes collecting, by a computing device, a set of biomarker and vital sign measurements of a population with a known clinical diagnosis. The method also includes determining, by the computing device, a statistical significance of each of the set of biomarker and vital sign measurements to the clinical diagnosis. The method also includes, for each of a plurality of different values n: selecting, by the computing device, a subset of the collected biomarker and vital sign measurements having the n highest statistical significances, and training, by the computing device, a plurality of machine learning models according to the selected subset of the collected biomarker and vital sign measurements. The method also includes determining, by the computing device, a performance characteristic of each of the machine learning models for each of the plurality of different values n. The method also includes providing, by the computing device to a second computing device, the machine learning model having the highest performance characteristic, wherein the machine learning module is associated with a selected subset of collected biomarker and vital sign measurements, and wherein the second computing device is configured to classify a sample according to the clinical diagnosis, via the provided machine learning model, the sample comprising the selected subset of collected biomarker and vital sign measurements for a subject.

In some implementations, the method includes training a plurality of machine learning models having different hyperparameter values according to the selected subset of the collected biomarker and vital sign measurements. In some implementations, the method includes training each machine learning model on a first portion of the collected biomarker and vital sign measurements, and validating each machine learning model on a second portion of the collected biomarker and vital sign measurements. In a further implementation, the first portion of the collected biomarker and vital sign measurements is balanced with respect to a known clinical diagnosis. In some implementations, the performance characteristic comprises an accuracy or sensitivity.

In another aspect, the present disclosure is directed to a method of treating sepsis. The method includes receiving, by a computing device, a set of biomarker and vital sign measurements of a subject having an unknown clinical diagnosis, the set of biomarker and vital sign measurements comprising measurements of a heart rate, a body temperature, a hemoglobin (HGB) count, a blood urea nitrogen (BUN) count, and a total carbon dioxide (TCO2) count. The method also includes classifying, by the computing device via a machine learning model, the subject as having sepsis responsive, the machine learning model trained from measurements of a heart rate, a body temperature, an HGB count, a BUN count, and a TCO2 count of subjects having a known clinical diagnosis; and responsive to the classification, treating the subject via plasmapheresis or plasma exchange. In some implementations, the machine learning model comprises a k-nearest neighbor (k-NN) algorithm, a neural network, a gradient boosting machine, a support vector machine, a logistic regression classifier, a naïve Bayes classifier, or a random forest classifier.

B. Computing Environment

Having discussed specific embodiments of the present solution, it may be helpful to describe aspects of the operating environment as well as associated system components (e.g., hardware elements) in connection with the methods and systems described herein.

Figure 6A:
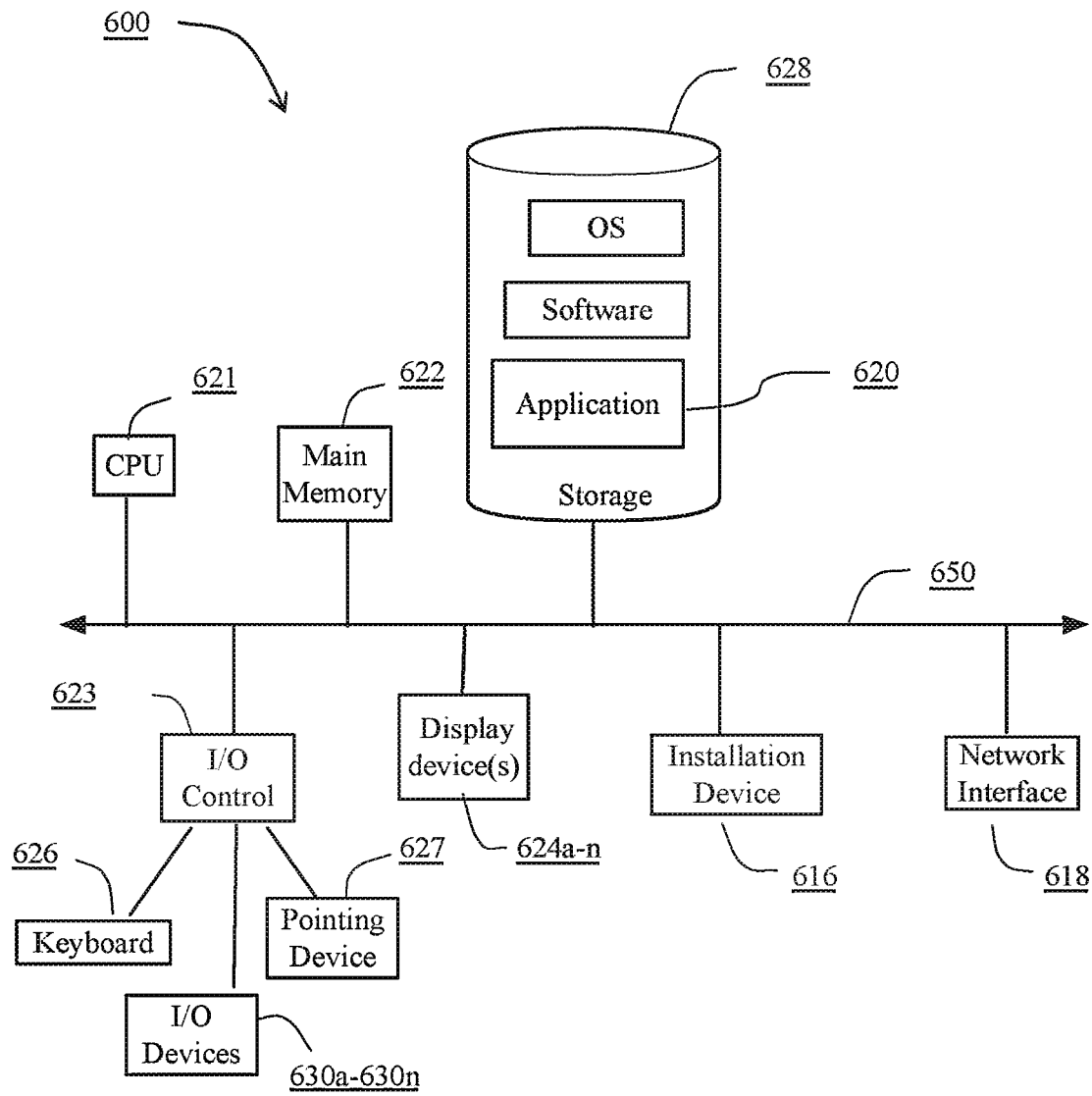
FIGS. 6A and 6B are block diagrams depicting embodiments of computing devices useful in connection with the methods and systems described herein.
Figure 6B:
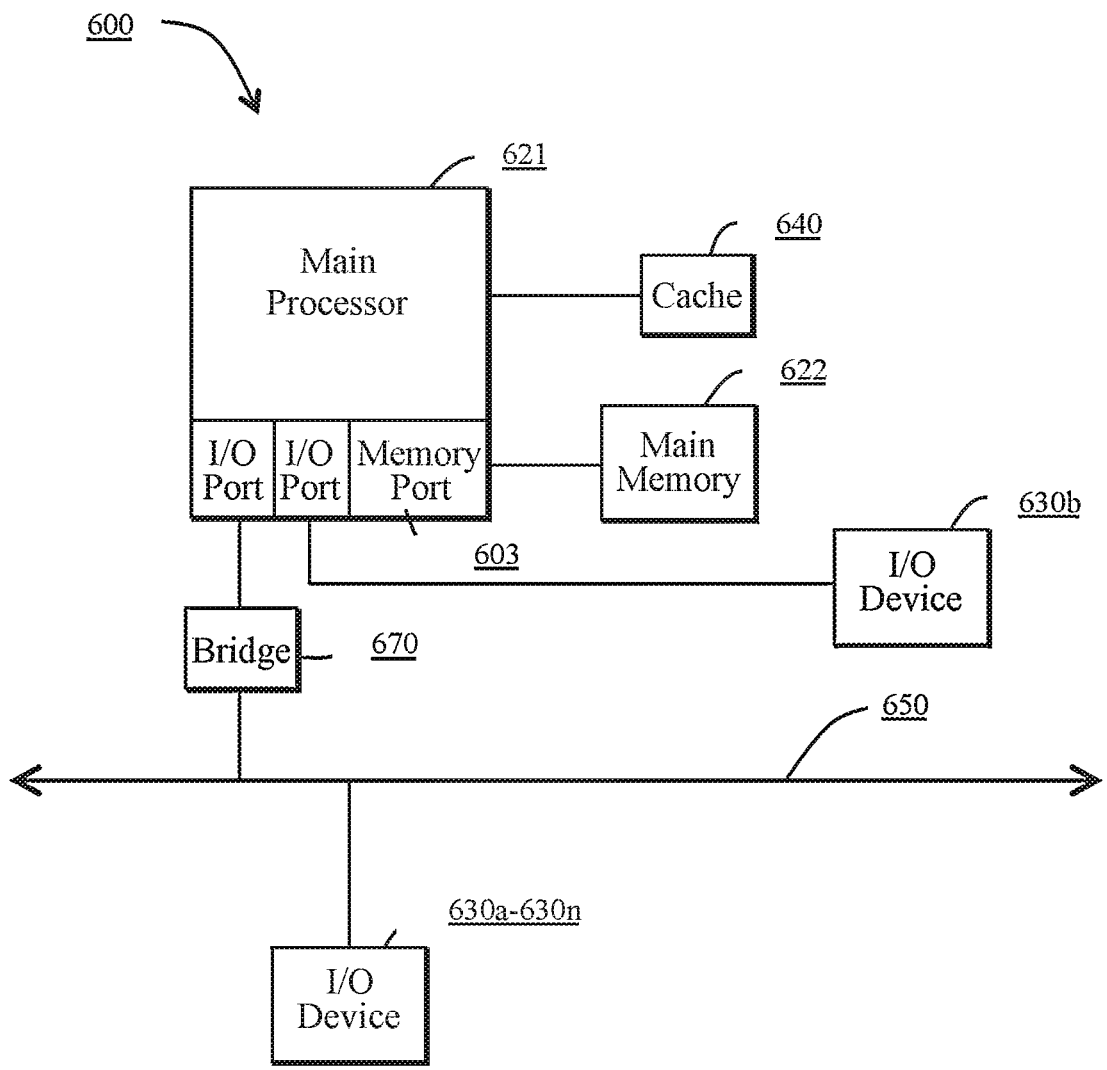

The systems discussed herein may be deployed as and/or executed on any type and form of computing device, such as a computer, network device or appliance capable of communicating on any type and form of network and performing the operations described herein. FIGS. 6A and 6B depict block diagrams of a computing device 600 useful for practicing an embodiment of the wireless communication devices 602 or the access point 606. As shown in FIGS. 6A and 6B, each computing device 600 includes a central processing unit 621, and a main memory unit 622. As shown in FIG. 6A, a computing device 600 may include a storage device 628, an installation device 616, a network interface 618, an I/O controller 623, display devices 624a-624n, a keyboard 626 and a pointing device 627, such as a mouse. The storage device 628 may include, without limitation, an operating system and/or software. As shown in FIG. 6B, each computing device 600 may also include additional optional elements, such as a memory port 603, a bridge 670, one or more input/output devices 630a-630n (generally referred to using reference numeral 630), and a cache memory 640 in communication with the central processing unit 621.

The central processing unit 621 is any logic circuitry that responds to and processes instructions fetched from the main memory unit 622. In many embodiments, the central processing unit 621 is provided by a microprocessor unit, such as: those manufactured by Intel Corporation of Mountain View, California; those manufactured by International Business Machines of White Plains, New York; or those manufactured by Advanced Micro Devices of Sunnyvale, California. The computing device 600 may be based on any of these processors, or any other processor capable of operating as described herein.

Main memory unit 622 may be one or more memory chips capable of storing data and allowing any storage location to be directly accessed by the microprocessor 621, such as any type or variant of Static random access memory (SRAM), Dynamic random access memory (DRAM), Ferroelectric RAM (FRAM), NAND Flash, NOR Flash and Solid State Drives (SSD). The main memory 622 may be based on any of the above described memory chips, or any other available memory chips capable of operating as described herein. In the embodiment shown in FIG. 6A, the processor 621 communicates with main memory 622 via a system bus 650 (described in more detail below). FIG. 6B depicts an embodiment of a computing device 600 in which the processor communicates directly with main memory 622 via a memory port 603. For example, in FIG. 6B the main memory 622 may be DRDRAM.

FIG. 6B depicts an embodiment in which the main processor 621 communicates directly with cache memory 640 via a secondary bus, sometimes referred to as a backside bus. In other embodiments, the main processor 621 communicates with cache memory 640 using the system bus 650. Cache memory 640 typically has a faster response time than main memory 622 and is provided by, for example, SRAM, BSRAM, or EDRAM. In the embodiment shown in FIG. 6B, the processor 621 communicates with various I/O devices 630 via a local system bus 650. Various buses may be used to connect the central processing unit 621 to any of the I/O devices 630, for example, a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 624, the processor 621 may use an Advanced Graphics Port (AGP) to communicate with the display 624. FIG. 6B depicts an embodiment of a computer 600 in which the main processor 621 may communicate directly with I/O device 630*b*, for example via HYPERTRANSPORT, RAPIDIO, or INFINIBAND communications technology. FIG. 6B also depicts an embodiment in which local busses and direct communication are mixed: the processor 621 communicates with I/O device 630*a* using a local interconnect bus while communicating with I/O device 630*b* directly.

A wide variety of I/O devices 630*a*-630*n* may be present in the computing device 600. Input devices include keyboards, mice, trackpads, trackballs, microphones, dials, touch pads, touch screen, and drawing tablets. Output devices include video displays, speakers, inkjet printers, laser printers, projectors and dye-sublimation printers. The I/O devices may be controlled by an I/O controller 623 as shown in FIG. 6A. The I/O controller may control one or more I/O devices such as a keyboard 626 and a pointing device 627, e.g., a mouse or optical pen. Furthermore, an I/O device may also provide storage and/or an installation medium 616 for the computing device 600. In still other embodiments, the computing device 600 may provide USB connections (not shown) to receive handheld USB storage devices such as the USB Flash Drive line of devices manufactured by Twintech Industry, Inc. of Los Alamitos, California.

Referring again to FIG. 6A, the computing device 600 may support any suitable installation device 616, such as a disk drive, a CD-ROM drive, a CD-R/RW drive, a DVD-ROM drive, a flash memory drive, tape drives of various formats, USB device, hard-drive, a network interface, or any other device suitable for installing software and programs. The computing device 600 may further include a storage device, such as one or more hard disk drives or redundant arrays of independent disks, for storing an operating system and other related software, and for storing application software programs such as any program or software 620 for implementing (e.g., configured and/or designed for) the systems and methods described herein. Optionally, any of the installation devices 616 could also be used as the storage device. Additionally, the operating system and the software can be run from a bootable medium.

Furthermore, the computing device 600 may include a network interface 618 to interface to the network 604 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, IEEE 802.11 ac, IEEE 802.11 ad, CDMA, GSM, WiMax and direct asynchronous connections). In one embodiment, the computing device 600 communicates with other computing devices 600' via any type and/or form of gateway or tunneling protocol such as Secure Socket Layer (SSL) or Transport Layer Security (TLS). The network interface 618 may include a built-in network adapter, network interface card, PCMCIA network card, card bus network adapter, wireless network adapter, USB network adapter, modem or any other device suitable for interfacing the computing device 600 to any type of network capable of communication and performing the operations described herein.

In some embodiments, the computing device 600 may include or be connected to one or more display devices 624*a*-624*n*. As such, any of the I/O devices 630*a*-630*n* and/or the I/O controller 623 may include any type and/or form of suitable hardware, software, or combination of hardware and software to support, enable or provide for the connection and use of the display device(s) 624*a*-624*n* by the computing device 600. For example, the computing device 600 may include any type and/or form of video adapter, video card, driver, and/or library to interface, communicate, connect or otherwise use the display device(s) 624*a*-624*n*. In one embodiment, a video adapter may include multiple connectors to interface to the display device(s) 624*a*-624*n*. In other embodiments, the computing device 600 may include multiple video adapters, with each video adapter connected to the display device(s) 624*a*-624*n*. In some embodiments, any portion of the operating system of the computing device 600 may be configured for using multiple displays 624*a*-624*n*. One ordinarily skilled in the art will recognize and appreciate the various ways and embodiments that a computing device 600 may be configured to have one or more display devices 624*a*-624*n*.

In further embodiments, an I/O device 630 may be a bridge between the system bus 650 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a FibreChannel bus, a Serial Attached small computer system interface bus, a USB connection, or a HDMI bus.

A computing device 600 of the sort depicted in FIGS. 6A and 6B may operate under the control of an operating system, which control scheduling of tasks and access to system resources. The computing device 600 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: Android, produced by Google Inc.; WINDOWS 7 and 8, produced by Microsoft Corporation of Redmond, Washington; MAC OS, produced by Apple Computer of Cupertino, California; WebOS, produced by Research In Motion (RIM); OS/2, produced by International Business Machines of Armonk, New York; and Linux, a freely-available operating system distributed by Caldera Corp. of Salt Lake City, Utah, or any type and/or form of a Unix operating system, among others.

The computer system 600 can be any workstation, telephone, desktop computer, laptop or notebook computer, server, handheld computer, mobile telephone or other portable telecommunications device, media playing device, a gaming system, mobile computing device, or any other type and/or form of computing, telecommunications or media device that is capable of communication. The computer system 600 has sufficient processor power and memory capacity to perform the operations described herein.

In some embodiments, the computing device 600 may have different processors, operating systems, and input devices consistent with the device. For example, in one embodiment, the computing device 600 is a smart phone, mobile device, tablet or personal digital assistant. In still other embodiments, the computing device 600 is an Android-based mobile device, an iPhone smart phone manufactured by Apple Computer of Cupertino, California, or a Blackberry or WebOS-based handheld device or smart phone, such as the devices manufactured by Research In Motion Limited. Moreover, the computing device 600 can be any workstation, desktop computer, laptop or notebook computer, server, handheld computer, mobile telephone, any other computer, or other form of computing or telecommunications device that is capable of communication and that has sufficient processor power and memory capacity to perform the operations described herein.

Although the disclosure may reference one or more "users", such "users" may refer to user-associated devices, for example, consistent with the terms "user" and "multi-user" typically used in the context of a multi-user multiple-input and multiple-output (MU-MIMO) environment.

It should be noted that certain passages of this disclosure may reference terms such as "first" and "second" in connection with devices, mode of operation, transmit chains, antennas, etc., for purposes of identifying or differentiating one from another or from others. These terms are not intended to merely relate entities (e.g., a first device and a second device) temporally or according to a sequence, although in some cases, these entities may include such a relationship. Nor do these terms limit the number of possible entities (e.g., devices) that may operate within a system or environment.

It should be understood that the systems described above may provide multiple ones of any or each of those components and these components may be provided on either a standalone machine or, in some embodiments, on multiple machines in a distributed system. In addition, the systems and methods described above may be provided as one or more computer-readable programs or executable instructions embodied on or in one or more articles of manufacture. The article of manufacture may be a floppy disk, a hard disk, a CD-ROM, a flash memory card, a PROM, a RAM, a ROM, or a magnetic tape. In general, the computer-readable programs may be implemented in any programming language, such as LISP, PERL, C, C++, C#, PROLOG, or in any byte code language such as JAVA. The software programs or executable instructions may be stored on or in one or more articles of manufacture as object code.

While the foregoing written description of the methods and systems enables one of ordinary skill to make and use what is considered presently to be the best mode thereof, those of ordinary skill will understand and appreciate the existence of variations, combinations, and equivalents of the specific embodiment, method, and examples herein. The present methods and systems should therefore not be limited by the above described embodiments, methods, and examples, but by all embodiments and methods within the scope and spirit of the disclosure.

We claim:

1. A method for training machine learning systems for early recognition of sepsis, comprising:
    collecting, by a computing device, a set of biomarker and vital sign measurements of a population with a known clinical diagnosis;
    applying, by the computing device, one or more transformations to each biomarker and vital sign measurement including standardization to create a modified set of biomarker and vital sign measurements;
    creating, by the computing device, a first training set comprising a subset of the modified set of biomarker and vital sign measurements;
    training, by the computing device, a machine learning system using the first training set; and
    validating, by the computing device, the machine learning system using a second subset of the modified set of biomarker and vital sign measurements as a test set.

2. The method of claim 1, further comprising:
    for each of a plurality of measurements of the subset, calculating a distance from a selected measurement of the subset;
    sorting each of the plurality of measurements of the subset based on an increasing order of distance from the selected measurement of the subset; and
    classifying a further subset of the subset based on the sorted distance as belonging to a first class.

3. The method of claim 2, wherein training the machine learning system further comprises using the classification of the further subset for a supervised learning process.

4. The method of claim 1, wherein applying the one or more transformations further comprises filtering samples from the collected set having incomplete biomarker or vital sign measurements.

5. The method of claim 1, wherein training the machine learning system further comprises training a plurality of machine learning systems with the first training set, and selecting a highest performing machine learning system of the plurality of machine learning systems.

6. The method of claim 5, wherein training the plurality of machine learning systems further comprises providing a first subset of the biomarker and vital sign measurements to a first machine learning system of the plurality of machine learning systems, and providing a different second subset of the biomarker and vital sign measurements to a second machine learning system of the plurality of machine learning systems.

7. The method of claim 6, wherein the first machine learning system and second machine learning system have identical hyperparameters.

8. The method of claim 5, wherein training the plurality of machine learning systems further comprises providing a first subset of the biomarker and vital sign measurements to each of a first machine learning system and a second machine learning system having different hyperparameters than the first machine learning system.

9. The method of claim 1, wherein creating the first training set further comprises selecting a first subset of the biomarker and vital sign measurements having a first known clinical diagnosis and a second subset of the biomarker and vital sign measurements having a second known clinical diagnosis, the second subset equal in number to the first subset.

10. A computing device comprising a processor executing a machine learning system trained according to the method of claim 1.

11. A method for machine learning-based identification of sepsis, comprising receiving, by a machine learning system trained according to the method of claim 1, a set of biomarker and vital sign measurements of a subject; and classifying, by the machine learning system, the subject as having sepsis.

12. The method of claim 11, wherein the machine learning system comprises a k-nearest neighbor (k-NN) classifier, a neural network, a gradient boosting machine, a support vector machine, a logistic regression classifier, a naïve Bayes classifier, or a random forest classifier.

13. The method of claim 11, wherein the set of biomarker and vital sign measurements of the subject consists essentially of measurements of a heart rate, a body temperature, a hemoglobin (HGB) count, a blood urea nitrogen (BUN) count, and a total carbon dioxide (TCO2) count.

14. A method for training machine learning systems for early recognition of sepsis, comprising:
collecting, by a computing device, a set of biomarker and vital sign measurements of a population with a known clinical diagnosis;
determining, by the computing device, a statistical significance of each of the set of biomarker and vital sign measurements to the clinical diagnosis;
for each of a plurality of different values n:
selecting, by the computing device, a subset of the collected biomarker and vital sign measurements having the n highest statistical significances, and
training, by the computing device, a plurality of machine learning models according to the selected subset of the collected biomarker and vital sign measurements;
determining, by the computing device, a performance characteristic of each of the machine learning models for each of the plurality of different values n; and providing, by the computing device to a second computing device, the machine learning model having the highest performance characteristic, wherein the machine learning module is associated with a selected subset of collected biomarker and vital sign measurements, and wherein the second computing device is configured to classify a sample according to the clinical diagnosis, via the provided machine learning model, the sample comprising the selected subset of collected biomarker and vital sign measurements for a subject.

15. The method of claim 14, wherein training the plurality of machine learning models further comprises training a plurality of machine learning models having different hyperparameter values according to the selected subset of the collected biomarker and vital sign measurements.

16. The method of claim 14, wherein training the plurality of machine learning models further comprises training each machine learning model on a first portion of the collected biomarker and vital sign measurements, and validating each machine learning model on a second portion of the collected biomarker and vital sign measurements.

17. The method of claim 16, wherein the first portion of the collected biomarker and vital sign measurements is balanced with respect to a known clinical diagnosis.

18. The method of claim 14, wherein the performance characteristic comprises an accuracy or sensitivity.

19. A method of treating sepsis, comprising:
receiving, by a computing device, a set of biomarker and vital sign measurements of a subject having an unknown clinical diagnosis, the set of biomarker and vital sign measurements comprising measurements of a heart rate, a body temperature, a hemoglobin (HGB) count, a blood urea nitrogen (BUN) count, and a total carbon dioxide (TCO2) count;
classifying, by the computing device via a machine learning model, the subject as having sepsis responsive, the machine learning model trained from measurements of a heart rate, a body temperature, an HGB count, a BUN count, and a TCO2 count of subjects having a known clinical diagnosis; and
responsive to the classification, treating the subject via plasmapheresis or plasma exchange.

20. The method of claim 19, wherein the machine learning model comprises a k-nearest neighbor (k-NN) algorithm, a neural network, a gradient boosting machine, a support vector machine, a logistic regression classifier, a naïve Bayes classifier, or a random forest classifier.

* * * * *